United States Patent [19]
Easley et al.

[11] Patent Number: 5,300,061
[45] Date of Patent: Apr. 5, 1994

[54] LASER DELIVERY PROBE HAVING A MECHANICALLY FREE FLOATING SHEATH

[75] Inventors: James C. Easley, St. Charles; Gregg D. Scheller, St. Louis, both of Mo.

[73] Assignee: Surgical Technologies, Inc., St. Louis, Mo.

[21] Appl. No.: 752,083

[22] Filed: Aug. 29, 1991

[51] Int. Cl.⁵ .............................................. A61B 17/36
[52] U.S. Cl. ............................................ 606/2; 606/4; 606/13; 606/16; 385/109
[58] Field of Search .................... 385/88, 92, 109, 117, 385/115, 116, 66, 68, 84, 86, 92, 147; 606/2, 4, 6, 7, 9, 10, 13–16; 219/121.6

[56] References Cited

U.S. PATENT DOCUMENTS

| | | | |
|---|---|---|---|
| 3,538,919 | 11/1970 | Meyer | 385/147 |
| 4,537,193 | 8/1985 | Tanner | 606/4 |
| 4,756,597 | 7/1988 | Hahn et al. | 385/117 |
| 5,129,895 | 7/1992 | Vassiliadis et al. | 606/6 |
| 5,151,962 | 9/1992 | Walker et al. | 385/86 |

FOREIGN PATENT DOCUMENTS

| | | | |
|---|---|---|---|
| 0152686 | 8/1985 | European Pat. Off. | 606/4 |
| 3232007 | 3/1983 | Fed. Rep. of Germany | 606/16 |

*Primary Examiner*—Stephen C. Pellegrino
*Assistant Examiner*—Jeffrey A. Schmidt
*Attorney, Agent, or Firm*—Polster, Lieder, Woodruff & Lucchesi

[57] ABSTRACT

A laser delivery probe includes a silica optical fiber extending generally from the distal to the proximal end of the probe, a laser connector adapted to be secured to a laser source, and a handpiece. The laser connector forms the proximal end of the probe and the handpiece forms the distal end. The optical fiber provides optical paths through the laser connector and the handpiece and is secured by adhesive to both. A sheath having a lumen in which the silica optical fiber is disposed terminates proximally inside the laser connector and terminating distally inside the handpiece. The sheath is mechanically free-floating with respect to the optical fiber so that torque applied to the optical fiber is not directly applied to the sheath. The probe is used in an anti-curl laser delivery system which also includes a laser source to which the laser connector is removably secured. The sheath damps curling movements caused by rotation of the handpiece.

5 Claims, 2 Drawing Sheets

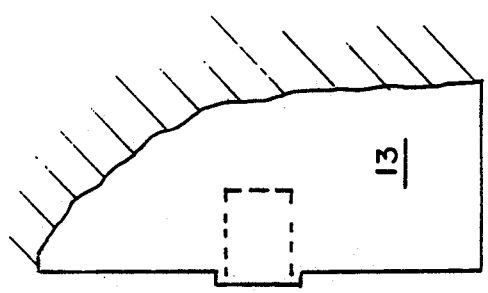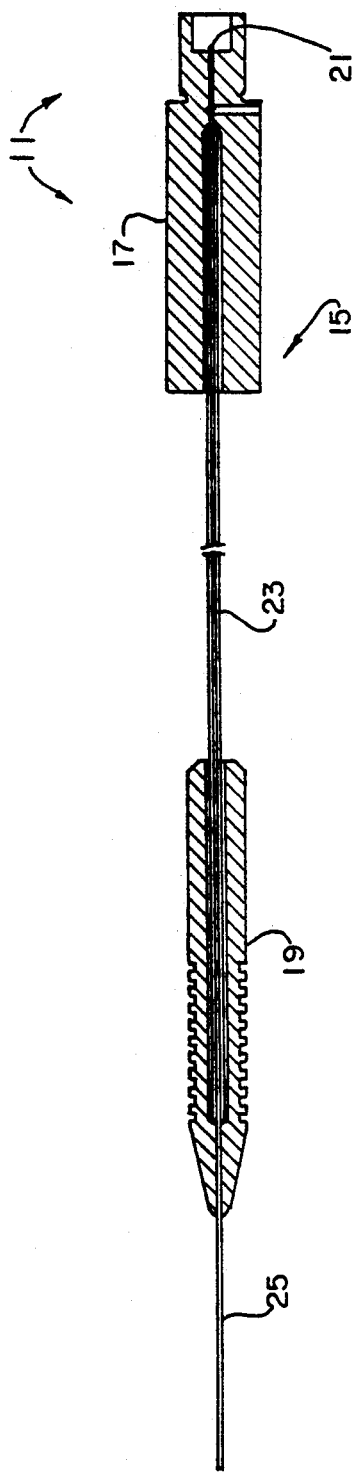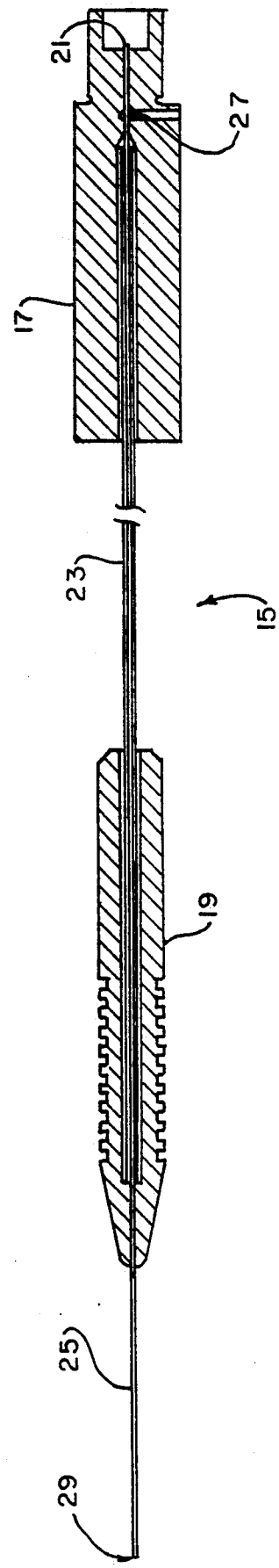
FIG.1.
FIG.2.

LASER DELIVERY PROBE HAVING A MECHANICALLY FREE FLOATING SHEATH

BACKGROUND OF THE INVENTION

The present invention relates to laser delivery systems and more particularly to such systems used in ophthalmic surgery and the like.

It is known that lasers may be used in ophthalmic surgery. Systems using lasers for this purpose typically include a laser source (which is disposed at some distance from the patient), an optical fiber cable (which can be eight feet or so in length) connected by a suitable connector to the laser source and extending from the laser source to the patient, and a handpiece in which the optical fiber cable terminates.

Prior laser probes—that part of the laser delivery system excluding the laser source itself—do an adequate job of transmitting the laser radiation from the laser source to the patient, but they could be improved. For example, it is often necessary in ophthalmic surgery to rotate the handpiece while performing the medical procedure. In fact, some handpieces (such as those with tips which are curved to allow laser application to remote ocular tissue structures) are designed with such a rotation in mind. The cables of prior art probes have a tendency, when such rotation occurs, to whip, twist or curl around, similar to the curling which occurs with an ordinary telephone cord. This twisting or curling, if severe, can result in the cable contacting a non-sterile surface and thus contaminating the sterile operating field.

Moreover, prior art probes tend to take a set while they are being stored prior to use. This set can also result in the cable contacting a non-sterile surface during a medical procedure.

Prior art probes also can cause undesirable forces to be applied to the handpiece during a procedure. These forces occur when the handpiece is moved proximally. The natural springiness of the cable can react against such movement, thereby tending to move the handpiece distally back into the eye.

SUMMARY OF THE INVENTION

Among the several objects and features of the present invention may be noted the provision of an improved laser delivery probe which is especially suited for ophthalmic surgery or the like.

Another object is the provision of such a probe which substantially eliminates the twisting or curling action of prior art probes.

A third object is the provision of such a probe which substantially eliminates the spring action of prior art probes.

A fourth object is the provision of such a probe with substantially improved handling characteristics.

A fifth object is the provision of such a probe which is reliable, yet relatively simple to manufacture.

Other objects and features will be in part apparent and in part pointed out hereinafter.

Briefly, a laser delivery probe of the present invention includes a silica optical fiber extending generally from the distal to the proximal end of the probe, a laser connector, and a handpiece. The laser connector is adapted to be secured to a laser source and forms the proximal end of the probe. The silica optical fiber extends substantially through the laser connector so that it provides an optical path through the laser connector. The handpiece is disposed at the distal end of the probe. The silica optical fiber extends substantially through the handpiece to provide an optical path through the handpiece. The optical fiber is fixedly secured to the laser connector and to the handpiece. A sheath having a lumen in which the silica optical fiber is disposed terminates proximally inside the laser connector and terminates distally inside the handpiece, The sheath is mechanically free-floating with respect to the optical fiber so that torque applied to the optical fiber is not directly applied to the sheath In addition, the sheath is manufactured from a material designed not to "set" when stored coiled. Moreover, the diameter and wall thickness of the sheath are minimized to facilitate minimal "setting" of the sheath.

The anti-curl laser delivery system of the present invention includes a laser source, and a laser delivery probe. The probe has a laser connector adapted to be removably securable to the laser source. The laser delivery probe also has a handpiece disposed at the proximal end thereof, and a silica optical fiber extending substantially the entire length of the laser delivery probe. A sheath is disposed over the silica optical fiber and extends into the laser connector and the handpiece. The sheath is mounted so as to damp curling or twisting movements caused by rotation of the handpiece.

BRIEF DESCRIPTION OF THE DRAWINGS

FIG. 1 is a side view with parts broken away for clarity of the laser delivery system of the present invention;

FIG. 2 is an enlarged sectional view of the laser delivery probe used in the system of FIG. 1.

Similar reference characters indicate similar parts throughout the several views of the drawings.

DESCRIPTION OF THE PREFERRED EMBODIMENT

Figure 3:
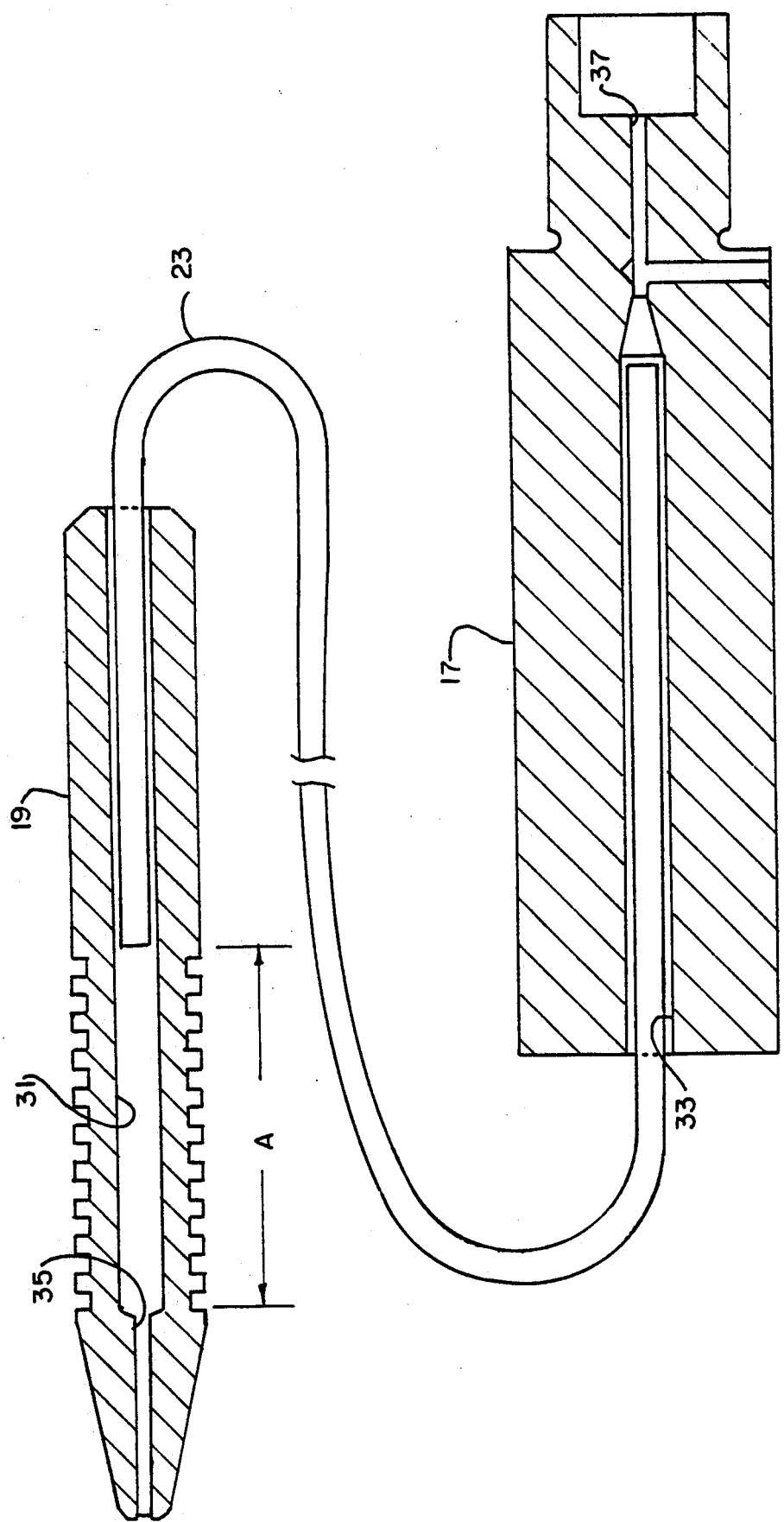
FIG. 3 is a sectional view, on a still larger scale, with parts removed for clarity, of the laser delivery probe of FIG. 2.

Turning to the drawings, a laser delivery system 11 of the present invention includes a laser source 13 (which can be any standard laser source) and a laser delivery probe 15. Probe 15 includes a laser connector 17 adapted to be removably securable to the laser source. Although a single-piece laser connector is shown, it should be understood that two-piece connectors, or other constructions could also be used without departing from the scope of the invention. Connector 17 is preferably made of a heat resistant material such as metal, ceramic or the like so that misalignment of the laser beam with the optical fiber does not damage the connector.

Laser delivery probe 15 also includes a handpiece 19 disposed at the proximal end thereof. A silica optical fiber 21 extends substantially the entire length of laser delivery probe 15. For most of the length of probe 15, silica optical fiber 21 is disposed in a plastic sheath 23 which is preferably black or opaque so as to provide light shielding for the optical fiber. Sheath 23, as is explained below, terminates inside laser connector 17 and handpiece 19, while optical fiber 21 continues past each end of the sheath. Distally, handpiece 19 terminates in a metal tube 25 in which is disposed the distal end of optical fiber 21 Although tube 25 is shown as straight, it should be understood that the distal end of tube 25 may be curved or bent in some applications.

Turning to FIG. 2, probe 1 5 is shown on a larger scale. Probe 15 is approximately eight feet in length. Optical fiber 21 extends substantially that entire length through the probe. It is glued to laser connector 17 at the point labelled 27 and is glued to the handpiece at the point labelled 29. The adhesive serves to fixedly secure the optical fiber in place against movement with respect to the handpiece and the laser connector.

It is neither necessary nor desired that the optical fiber be secured in place with respect to sheath 23. Although the optical fiber is disposed in the lumen of sheath 23, the sheath is mechanically free-floating with respect to the optical fiber, the handpiece, and the laser connector. As a result, motions of the handpiece and optical fiber are transmitted poorly to the sheath. Stated another way, sheath 23 is mounted so as to damp twisting or curling movements caused by rotation of handpiece 19.

In addition, sheath 23 is manufactured from a material (50 durometer PVC) which does not tend to take a "set." Probe sets are typically coiled in an individual pouch to reduce the overall dimensions of the product during shipping and storage. Prior art sheaths tended to take a "set" during this time, with the result that the "telephone cord" effect was accentuated. Sheath 23 is designed to substanially eliminate that effect by reason of the material from which it is constructed. Other materials having the same feature could be used instead.

To further reduce the tendency to take a "set," the outside diameter and wall thickness of sheath 23 are also reduced to a minimum. For example, an outer diameter of 0.07 inch with a wall thickness of 0.03 inch has been found to provide satisfactory performance. This construction, in combination with the material making up sheath 23, practically eliminates any tendency of the sheath to take a "set" while coiled during storage.

It has been found that with prior art probes, one or two rotations of the handpiece will result in significant flopping and twisting of the optical cable (optical fiber plus sheath). With the present construction, such twisting does not occur until the handpiece has been twisted twelve times or so. This is a result of the loose coupling between the sheath and the other components of the probe, and the damping action of the sheath.

With any laser delivery system, the rotation of the handpiece eventually affects the optical cable, since the laser connector is fixedly secured to the laser source. The present construction, however, significantly reduces that effect.

In addition to reducing the effect of rotational motion on the optical cable, the present construction reduces the springing effect resulting from axial motion of the handpiece in prior systems. The springing effect is reduced in part by reason of the material making up sheath 23, and in part because of the relatively small cross-sectional area of the sheath as compared to prior art sheaths. Both result in a sheath which is more flexible than prior designs. In addition, the reduction in springing is also a function of the fact that the sheath is not fixedly mounted at either end. This is illustrated in FIG. 3. In this Fig., the distal tube 25 and silica optical fiber 21 have been removed for clarity to illustrate this aspect of the present invention.

As can be seen in FIG. 3, sheath 23 is disposed in a first handpiece bore 31 in handpiece 19 and in a first connector bore 33 in connector 17. The total distance between the distal end of handpiece 19 and the proximal end of laser connector 17 is fixed because of optical fiber 21 being fixedly secured to each. But sheath 23 is not fixed to either. The sheath is longitudinally free to move with respect to the handpiece over at least a predetermined axial distance labelled "A" in FIG. 3.

As a result, when handpiece is moved proximally, sheath 23 moves in the available space rather than exert a force opposing that proximal motion. It should be appreciated that the optical fiber itself does generate such an opposing force, but due to the much smaller cross-sectional area of the optical fiber as compared to that of the sheath, that opposing force is much smaller than that occurring in the prior art devices.

Similarly, since the sheath is not fixed to any of the other components of the probe, it is also longitudinally free to move with respect to the laser connector over the predetermined axial distance "A".

Eventually, relative motion of sheath 23 is stopped by reason of smaller bores 35 and 37 at the respective ends of the handpiece and laser connector. Bores 35 and 37 are sized to receive tube 25 and optical fiber 21 respectively.

The present construction, therefore, while relatively simple, results in significant functional advantages. The rotational motion of the handpiece, which in prior devices results in unacceptable flopping or twisting of the optical cable, has no deleterious effect at all for amounts of rotation normally encountered. In addition, axial movement of the handpiece is accommodated by the sheath without the undesirable "spring" action of prior devices.

In view of the above, it will be seen that the various objects and features of the present invention are achieved and other advantageous results obtained. The embodiments and constructions disclosed herein are intended to be illustrative and are not to be taken in a limiting sense.

What is claimed is:

1. A laser delivery probe comprising:
    a silica optical fiber extending generally from a distal end of the probe to a proximal end of the probe;
    a laser connector adapted to be secured to a laser source, said laser connector forming the proximal end of the probe, said silica optical fiber extending substantially through the laser connector so that the optical fiber provides an optical path through the laser connector;
    a handpiece disposed at the distal end of the probe, said silica optical fiber extending substantially through the handpiece to provide an optical path through the handpiece;
    means for fixedly securing the optical fiber to the laser connector to hold the optical fiber fixedly in place with respect to the laser connector;
    means for fixedly securing the optical fiber to the handpiece to hold the optical fiber fixedly in place with respect to the handpiece;
    a sheath having a lumen in which the silica optical fiber is disposed, said sheath terminating proximally inside the laser connector and terminating distally inside the handpiece, said sheath being mechanically free-floating with respect to the optical fiber so that torque applied to the optical fiber is not directly applied to the sheath;

2. A laser delivery probe comprising:
    a silica optical fiber extending generally from a distal end of the probe to a proximal end of the probe;

a laser connector adapted to be secured to a laser source, said laser connector forming the proximal end of the probe, said silica optical fiber extending substantially through the laser connector so that the optical fiber provides an optical path through the laser connector;

a handpiece disposed at the distal end of the probe, said silica optical fiber extending substantially through the handpiece to provide an optical path through the handpiece;

means for fixedly securing the optical fiber t the laser connector to hold the optical fiber fixedly in place with respect to the laser connector;

means for fixedly securing the optical fiber to the handpiece to hold the optical fiber fixedly in place with respect to the handpiece;

a sheath having a lumen in which the silica optical fiber is disposed, said sheath terminating proximally inside the laser connector and terminating distally inside the handpiece, said sheath being mechanically free-floating with respect to the optical fiber so that torque applied to the optical fiber is not directly applied to the sheath;

wherein the sheath is longitudinally free to move with respect to the laser connector over at least a predetermined axial distance.

3. The laser delivery probe as set forth in claim 2 wherein the sheath is longitudinally free to move with respect to the handpiece over at least a predetermined axial distance.

4. An anti-curl laser delivery system comprising:
a laser source;
a laser delivery probe having a laser connector adapted to be removably securable to the laser source, said laser delivery probe having a proximal end and a distal end;
said laser delivery probe also having a handpiece disposed at the distal end thereof, and a silica optical fiber extending substantially the entire length of the laser delivery probe;
a sheath disposed over the silica optical fiber and extending into the laser connector and the handpiece, said sheath being mounted so as to damp curling movements caused by rotation of the handpiece;
wherein the sheath is mechanically free-floating with respect to the laser connector and the handpiece.

5. The anti-curl laser delivery system as set forth in claim 4 wherein the sheath is mechanically free-floating with respect to the optical silica fiber.

* * * * *